United States Patent [19]

Goto et al.

[11] Patent Number: 5,346,880
[45] Date of Patent: Sep. 13, 1994

[54] HERBICIDALLY ACTIVE PYRIMIDINYLTHIOALKANE DERIVATIVES

[75] Inventors: Toshio Goto, Kokubunkji; Yoshinori Kitagawa, Moka; Hidenori Hayakawa, Oyama; Katsuhiko Shibuya, Oyama; Ryo Watanabe, Oyama, all of Japan

[73] Assignee: Nihon Bayer Agrochem K.K., Tokyo, Japan

[21] Appl. No.: 43,513

[22] Filed: Apr. 6, 1993

[30] Foreign Application Priority Data

Apr. 13, 1992 [JP] Japan ................................ 4-118540
Jun. 30, 1992 [JP] Japan ................................ 4-194529
Sep. 11, 1992 [JP] Japan ................................ 4-267865

[51] Int. Cl.$^5$ .................. A01N 43/54; C07D 239/47; C07D 239/56; C07D 239/60
[52] U.S. Cl. .................. 504/242; 504/243; 544/301; 544/302; 544/311; 544/314; 544/316; 544/318; 544/313
[58] Field of Search ............... 544/301, 302, 311, 314, 544/316, 318, 313; 504/242, 243

[56] References Cited

U.S. PATENT DOCUMENTS 5,087,289 2/1992 Kaku et al. ........................ 544/212

FOREIGN PATENT DOCUMENTS 2021486 1/1991 Canada .
0400741 12/1990 European Pat. Off. .

OTHER PUBLICATIONS

Derwent Abstract of Japanese 24077/1991.
Derwent Abstract of Japanese 135963/1991.

*Primary Examiner*—John M. Ford
*Attorney, Agent, or Firm*—Sprung Horn Kramer & Woods

[57] ABSTRACT

This invention relates to novel pyrimidinylthioalkane derivatives of the formula

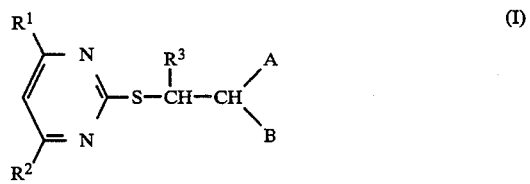

wherein $R^1$, $R^2$ and $R^3$ are defined in the specification and A represents hydroxy, and B represents hydrogen or A and B together form a carbonyl group, a process for their production and a method of using said derivatives to combat unwanted plant growth.

8 Claims, No Drawings

HERBICIDALLY ACTIVE PYRIMIDINYLTHIOALKANE DERIVATIVES

The present invention relates to novel pyrimidinylthioalkane derivatives, to processes for their preparation and to their use as herbicides.

It has already been disclosed that a certain group of compounds having a pyrimidinylthio group has herbicidal properties. (See Japanese Patent Laid-open Nos. 85262/1990, 135963/1991 and 240777/1991).

There have now been found novel pyrimidinylthioalkane derivatives of the general formula (I)

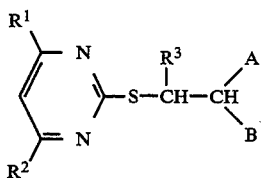

wherein $R^1$ represents $C_1$-$C_4$-alkyl, $C_1$-$C_4$-alkoxy, halo, $C_1$-$C_4$-haloalkyl or $C_1$-$C_4$-haloalkoxy, $R^2$ represents $C_1$-$C_4$-alkyl, $C_1$-$C_4$-alkoxy, halogen, $C_1$-$C_4$-haloalkyl or $C_1$-$C_4$-haloalkoxy, $R^3$ represents straight chain or branched $C_1$-$C_{30}$-alkyl optionally substituted by $C_3$-$C_8$-cycloalkyl, halogen, naphthyl or optionally substituted phenyl; phenyl optionally substituted by halogen, $C_1$-$C_4$-alkyl, $C_1$-$C_4$-haloalkyl, nitro or cyano; naphthyl; or $C_3$-$C_8$-cycloalkyl, and A represents hydroxy, and B represents hydrogen, or A and B together are=O.

The compounds of the general formula (I) can be obtained by a process in which a) where A and B form carbonyl, a compound of the formula (II)

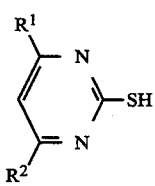

wherein $R^l$ and $R^2$ have the above-mentioned meanings, is reacted with a compound of the formula (III)

wherein X is halogen, in an inert solvent and, if appropriate, in the presence of an acid binder, b) where A and B form carbonyl, a compound of the formula (Ia)

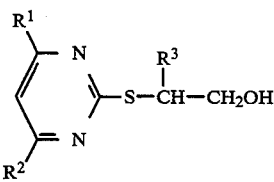

is reacted with an oxidizing agent in an inert solvent; or c) where A is hydroxy and B is hydrogen, a compound of the formula (Ib)

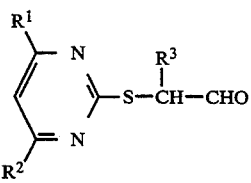

is reacted with a reducing agent in an inert solvent; or d) where A is hydroxy and B is hydrogen, a compound of the formula (IV)

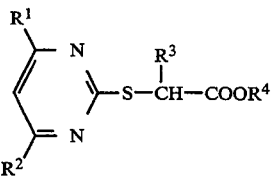

(IV)

wherein $R^4$ is hydrogen or alkyl, is reacted with a reducing agent in an inert solvent; or e) where A is hydroxy and B is hydrogen, a compound of the formula (V)

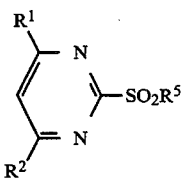

(V)

wherein $R^5$ is alkyl or benzyl, is reacted with a compound of the formula (VI)

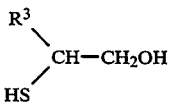

(VI)

in an inert solvent and, if appropriate, in the presence of a base; or f) where A is hydroxy and B is hydrogen, a compound of the formula (VII)

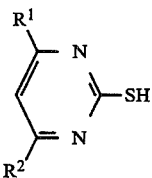

is reacted with a compound of the formula (VIII)

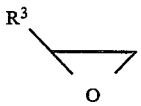

in an inert solvent; or g) where A is hydroxy and B is hydrogen, a compound of the formula (VII) is reacted with a compound of the formula (IX)

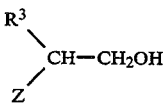

wherein Z is halogen, in an inert solvent and, if appropriate, in the presence of a base.

The pyrimidinylthioalkane derivatives exhibit herbicidal properties.

In the formulae, $C_1$-$C_4$-alkyl and the alkyl parts in $C_1$-$C_4$-alkoxy, halo-$C_1$-$C_4$-alkyl and halo-$C_1$-$C_4$-alkoxy represent methyl, ethyl, propyl, isopropyl, or (n-, iso-, sec- or tert-) butyl, preferably methyl or ethyl;

halo and the halo parts in halo-$C_1$-$C_4$-alkyl and halo-$C_1$-$C_4$-alkoxy represent fluorine, chlorine, bromine or iodine, preferably fluorine, chlorine or bromine; $C_3$-$C_8$-cycloalkyl represents preferably cyclopropyl, cyclopentyl or cyclohexyl; and $C_1$-$C_{30}$-alkyl represents, besides the aforementioned $C_1$-$C_4$-alkyl, straight chain alkyl such as n-pentyl, n-hexyl, n-heptyl, n-octyl, n-nonyl, n-decyl, n-undecyl or n-dodecyl, or branched chain alkyl such as iso-pentyl, 1-methylbutyl, 1-methylpentyl, 1-methylhexyl, 1-methylheptyl or 1-methyloctyl.

Among the compounds of the formula (I), according to the invention, preferred compounds are those wherein $R^1$ represents $C_1$-$C_3$-alkyl, $C_1$-$C_3$-alkoxy, fluorine, chlorine, bromine, iodine, $C_1$-$C_3$-haloalkyl or $C_1$-$C_3$-haloalkoxy, $R^2$ represents $C_1$-$C_3$-alkyl, $C_1$-$C_3$-alkoxy, fluorine, chlorine, bromine, iodine, $C_1$-$C_3$-haloalkyl or $C_1$-$C_3$-haloalkoxy, $R^3$ represents straight chain or branched $C_1$-$C_{12}$-alkyl optionally substituted by $C_3$-$C_6$-cycloalkyl, fluorine, chlorine, bromine, $C_1$-$C_4$-alkylphenyl, halophenyl, or $C_{1-4}$-alkoxyphenyl, phenyl which is optionally substituted by $C_1$-$C_4$-alkyl, halogen, or $C_1$-$C_4$-haloalkyl (wherein halo is chlorine or bromine), nitro or cyano; or $C_3$-$C_6$-cycloalkyl, and A represents hydroxy, and B represents hydrogen, or A and B together are=0.

Particularly preferred compounds of the general formula (I) are those wherein $R^1$ represents methyl, ethyl, methoxy, ethoxy, fluorine, chlorine, bromine, trichloromethyl, trifluoromethyl, chloromethoxy, difluoromethoxy or trifluoromethoxy, $R^2$ represents methyl, ethyl, methoxy, fluorine, chlorine, bromine, trichloromethyl, trifluoromethyl, chloromethoxy, difluoromethoxy or trifluoromethoxy, $R^3$ represents straight chain or branched $C_1$-$C_{10}$-alkyl optionally substituted by $C_3$-$C_6$-cycloalkyl, fluorine, chlorine, bromine, chlorophenyl, $C_1$-$C_4$-alkylphenyl, or methoxyphenyl, optionally substituted phenyl which may be substituted by $C_{1-4}$-alkyl, chlorophenyl, $C_{1-3}$haloalkyl or nitro, or $C_{5-6}$-cycloalkyl, and A represents hydroxy, and B represents hydrogen, or A and B together are=0.

Very particularly preferred compounds of the general formula (I) are those in which $R^1$ and $R^2$ are methoxy, $R^3$ represents straight chain or branched $C_{1-9}$-alkyl optionally substituted by at least one member selected from the group consisting of cyclopropyl, cyclopentyl, cyclohexyl, fluorine, chlorine, bromine, chlorophenyl, $C_{1-4}$-alkyl-substituted phenyl and methoxyphenyl, optionally substituted phenyl which may be substituted by at least one selected from a group consisting of methyl, tert.-butyl, chlorine, trifluoromethyl and nitro, cyclopentyl, or cyclohexyl, A is hydroxy, and B is hydrogen, or A and B together are=0.

As exampes of the compounds of the formula (I), besides those mentioned in examples hereinafter, the following can be enumerated:

2-(4,6-dimethoxy-2-pyrimidinylthio)-3-methylbutyraldehyde, 2-(4,6-dimethoxy-2-pyrimidinylthio)propionaldehyde, 2-(4,6-dimethoxy-2-pyrimidinylthio)butyraldehyde, 2-(4,6-dimethoxy-2-pyrimidinylthio)valeraldehyde.

2-(4,6-dimethoxy-2-pyrimidinylthio)hexylaldehyde, 2-(4,6-dimethoxy-2-pyrimidinylthio)-4-methylvaleraldehyde, 2-(4,6-dimethoxy-2-pyrimidinylthio)-3-methylvaleraldehyde, 2-(4,6-dimethoxy-2-pyrimidinylthio)-3,3-dimethylbutyraldehyde, 2-(4,6-dimethoxy-2-pyrimidinylthio)heptaldehyde, 2-(4,6-dimethoxy-2-pyrimidinylthio)-5-methylhexaldehyde, 2-(4,6-dimethoxy-2-pyrimidinylthio)-3-methylhexaldehyde, 2-(4,6-dimethoxy-2-pyrimidinylthio)octylaldehyde, 2-(4,6-dimethoxy-2-pyrimidinylthio)-3-methylheptaldehyde, 2-(4,6-dimethoxy-2-pyrimidinylthio)nonylaldehyde, 2-(4,6-dimethoxy-2-pyrimidinylthio)-3-methyloctylaldehyde, 2-(4,6-dimethoxy-2-pyrimidinylthio)-3,5,5-trimethylhexaldehyde, 2-(4,6-dimethoxy-2-pyrimidinylthio)decylaldehyde, 2-(4,6-dimethoxy-2-pyrimidinylthio)-3-methylnonylaldehyde, 2-(4,6-dimethoxy-2-pyrimidinylthio)undecylaldehyde, 2-(4,6-dimethoxy-2-pyrimidinylthio)-3-methyldecylaldehyde, 3-cyclopentyl-2-(4,6-dimethoxy-2-pyrimidinylthio)-propionaldehyde,
3-cyclopentyl-2-(4,6-dimethoxy-2-pyrimidinylthio)-butyraldehyde,
3-cyclohexyl-2-(4,6-dimethoxy-2-pyrimidinylthio)propionaldehyde,
3-cyclohexyl-2-(4,6-dimethoxy-2-pyrimidinylthio)-butyraldehyde,
2-cyclopentyl-2-(4,6-dimethoxy-2-pyrimidinylthio)acetaldehyde,
2-cyclohexyl-2-(4,6-dimethoxy-2-pyrimidinylthio)acetaldehyde,
4,4,4-trifluoro-2-(4,6-dimethoxy-2-pyrimidinylthio)-butyraldehyde,
4-bromo-2-(4,6-dimethoxy-2-pyrimidinylthio)-butyraldehyde,
2-(4,6-dimethoxy-2-pyrimidinylthio)-3-phenylpropionaldehyde,
2-(4,6-dimethoxy-2-pyrimidinylthio)-3-phenylbutyraldehyde,
3-(4-chlorophenyl)-2-(4,6-dimethoxy-2-pyrimidinylthio)propionaldehyde,
3-(4-chlorophenyl)-2-(4,6-dimethoxy-2-pyrimidinylthio)butyraldehyde,
3-(4-tert.-butylphenyl)-2-(4,6-dimethoxy-2-pyrimidinylthio)propionaldehyde,
3-(2-chlorophenyl)-2-(4,6-dimethoxy-2-pyrimidinylthio)butyraldehyde,
2-(4,6-dimethoxy-2-pyrimidinylthio)-4-phenylvaleraldehyde,
2-(4,6-dimethoxy-2-pyrimidinylthio)-3-(2,6-dimethylphenyl)propionaldehyde,
2-(4,6-dimethoxy-2-pyrimidinylthio)-2-phenylacetaldehyde,
2-(4,6-dimethoxy-2-pyridmiinylthio)-2-(4-methylphenyl)acetaldehyde,
2-(4-tert.-butylphenyl)-2-(4,6-dimethoxy-2-pyrimidinylthio)acetaldehyde,
2-(4,6-dimethoxy-2-pyrimidinylthio)-2-(2,6-dimethylphenyl)acetaldehyde,
2-(4-chlorophenyl)-2-(4,6-dimethoxy-2-pyrimidinylthio)acetaldehyde,
2-(4,6-dimethoxy-2-pyrimidinylthio)-2-(4-nitrophenyl)acetaldehyde,
2-(4-trifluoromethylphenyl)-2-(4,6-dimethoxy-2-pyrimidinylthio)acetaldehyde,
2-(4-cyanophenyl)-2-(4,6-dimethoxy-2-pyrimidinylthio)acetaldehyde,
2-[4,6-bis(difluoromethoxy)-2-pyrimidinylthio]propionaldehyde,
2-(4-methyl-6-trifluoromethyl-2-pyrimidinylthio)propionaldehyde,
2-(4-chloro-6-methoxy-2-pyrimidinylthio)propionaldehyde,
2-(2-fluorophenyl)-2-(4,6-dimethoxy-2-pyrimidinylthio)acetaldehyde,
2-(3-fluorophenyl)-2-(4,6-dimethoxy-2-pyrimidinylthio)acetaldehyde,
2-(4-fluorophenyl)-2-(4,6-dimethoxy-2-pyrimidinylthio)acetaldehyde,
2-(2-chlorophenyl)-2-(4,6-dimethoxy-2-pyrimidinylthio)acetaldehyde,
2-(3-chlorophenyl)-2-(4,6-dimethoxy-2-pyrimidinylthio)acetaldehyde,
2-(2-bromophenyl)-2-(4,6-dimethoxy-2-pyrimidinylthio)acetaldehyde,
2-(3-bromophenyl)-2-(4,6-dimethoxy-2-pyrimidinylthio)acetaldehyde,
2-(4-bromophenyl)-2-(4,6-dimethoxy-2-pyrimidinylthio)acetaldehyde,
2-(2,4-dichlorophenyl)-2-(4,6-dimethoxy-2-pyrimidinylthio)acetaldehyde,
2-(4,6-dimethoxy-2-pyrimidinylthio)-2-(2-methylphenyl)acetaldehyde,
2-(4,6-dimethoxy-2-pyrimidinylthio)-2-(3-methylphenyl)acetaldehyde,
2-(4-cyanophenyl)-2-(4,6-dimethoxy-2-pyrimidinylthio)acetaldehyde,
2-(4,6-dimethoxy-2-pyrimidinylthio)-2-(2-naphthyl)acetaldehyde,
3-ethyl-2-(4,6-dimethoxy-2-pyrimidinylthio)valeraldehyde,
3-ethyl-2-(4,6-dimethoxy-2-pyrimidinylthio)-3-methylvaleraldehyde,
2-(4,6-dimethoxy-2-pyrimidinylthio)-3,3-dimethylheptaldehyde,
2-(4,6-dimethoxy-2-pyrimidinylthio)-3,3-dimethylvaleraldehyde,
2-(4,6-dimethoxy-2-pyrimidinylthio)-3,3-dimethyl-5phenylvaleraldehyde,
2-(4,6-dimethoxy-2-pyrimidinylthio)-3-phenylvaleraldehyde,
2-(4,6-dimethoxy-2-pyrimidinylthio)-4-methyl-3-phenylvaleraldehyde,
2-(4,6-dimethoxy-2-pyrimidinylthio)-3-methyl-3-phenylbutyraldehyde,
2-(4,6-dimethoxy-2-pyrimidinylthio)-3-methyl-3-phenylvaleraldehyde,
3-ethyl-2-(4,6-dimethoxy-2-pyrimidinylthio)-3-phenylvaleraldehyde,
3-(2-chlorophenyl)-2-(4,6-dimethoxy-2-pyrimidinylthio)-3-methylbutyraldehyde,
3-(3-chlorophenyl)-2-(4,6-dimethoxy-2-pyrimidinylthio)-3-methylbutyraldehyde,
2-(4,6-dimethoxy-2-pyrimidinylthio)-4-phenylbutyraldehyde,
2-(4,6-dimethoxy-2-pyrimidinylthio)-3,3-dimethyloctylaldehyde,
3-(3-chlorophenyl)-2-(4,6-dimethoxy-2-pyrimidinylthio)-3methylbutyraldehyde,
3-(4-bromophenyl)-2-(4,6-dimethoxy-2-pyrimidinylthio)-3-methylbutyraldehyde,
2-(4,6-dimethoxy-2-pyrimidinylthio)-3-methyl-3-(2-methylphenyl)butyraldehyde,
2-(4,6-dimethoxy-2-pyrimidinylthio)-3-methyl-3-(3-methylphenyl)butyraldehyde,
2-(4,6-dimethoxy-2-pyrimidinylthio)-3-methyl-3-(4-methylphenyl)butyraldehyde,
2-(4,6-dimethoxy-2-pyrimidinylthio)-3-methyl-3-(4-nitrophenyl)butyraldehyde,
2-(4,6-dimethoxy-2-pyrimindinylthio)-2-(1-phenylcyclopentyl)acetaldehyde,
3-(3-bromophenyl)-2-(4,6-dimethoxy-2-pyrimidinylthio)-3-methylbutyraldehyde,
3-(2-fluorophenyl)-2-(4,6-dimethoxy-2-pyrimindinylthio)-3-methylbutyraldehyde,
3-(4-fluorophenyl)-2-(4,6-dimethoxy-2-pyrimidinylthio)-3-methylbutyraldehyde,
3-(2,6-dicholorophenyl)-2-(4,6-dimethoxy-2-pyrimidinylthio)propionaldehyde,
2-(4,6-dimethoxy-2-pyrimidinylthio)-3-(2-methylphenyl)propionaldehyde,
3-(2,4-dichlorophenyl)-2-(4,6-dimethoxy-2-pyrimidinylthio)-3-methylbutyraldehyde,
2-(4,6-dimethoxy-2-pyrimidinylthio)-3-(2-methylphenyl)butyraldehyde, 3-(3,4-dichlorophenyl)-2-(4,6-dimethoxy-2-pyrimidinylthio)-3-methylbutyraldehyde,
3-(3,4-difluorophenyl)-2-(4,6-dimethoxy-2-pyrimidinylthio)-3-methylbutyraldehyde,
3(2,5-difluorophenyl)-2-(4,6-dimethoxy-2-pyrimidinylthio))-3-methylbutyraldehyde,
2-(4,6-dimethoxy-2-pyrimidinylthio)-3-methyl-3-(2,4-xylyl)butyraldehyde,
3(2,6-diethylphenyl)-2-(4,6-dimethoxy-2-pyrimidinylthio)propionaldehyde,
3-(3-trifluoromethylphenyl)-2-(4,6-dimethoxy-2-pyrimidinylthio)-3-methylbutyraldehyde,
3(3-fluorophenyl)-2-(4,6-dimethoxy-2-pyrimidinylthio)-3-methylbutyraldehyde,
2-(4,6-dimethoxy-2-pyrimidinylthio)-3-methyl-3-(2-naphthyl)butyraldehyde,
3-(cyclopropyl)-2-(4,6-dimethoxy-2-pyrimidinylthio)propionaldehyde,
2-(4,6-dimethoxy-2-pyrimidinylthio)-2-(2-methylcyclopentyl)acetaldehyde,
2-(4,6-dimethoxy-2-pyrimidinylthio)-2-(3-methylcyclopentyl)acetaldehyde,
2-(4,6-dimethoxy-2-pyrimidinylthio)-2-(2,4-dimethylcyclopentyl)acetaldehyde,
2-cyclobutyl-2-(4,6-dimethoxy-2-pyrimidinylthio)acetaldehyde,
4-chloro-2-(4,6-dimethoxy-2-pyrimidinylthio)butyraldehyde,
2-(4,6-dimethoxy-2-pyrimidinylthio)propanol,
2-(4,6-dimethoxy-2-pyrimidinylthio)butanol,
2-(4,6-dimethoxy-2-pyrimidinylthio)pentanol,
2-(4,6-dimethoxy-2-pyrimidinylthio)-3-methylbutanol,
2-(4,6-dimethoxy-2-pyrimidinylthio)hexanol,
2-(4,6-dimethoxy-2-pyrimidinylthio)-4-methylpentanol,
2-(4,6-dimethoxy-2-pyrimidinylthio)-3-methylpentanol,
2-(4,6-dimethoxy-2-pyrimidinylthio)-3,3-dimethylbutanol,
2-(4,6-dimethoxy-2-pyridmidinylthio)heptanol,
2-(4,6-dimethoxy-2-pyrimidinylthio)-5-methylhexanol,
2-(4,6-dimethoxy-2-pyrimidinylthio)-3-methylhexanol,
2-(4,6-dimethoxy-2-pyrimidinylthio)octanol,
2-(4,6-dimethoxy-2-pyrimidinylthio)-3-methylheptanol,
2-(4,6-dimethoxy-2-pyrimidinylthio)nonanol,
2-(4,6-dimethoxy-2-pyrimidinylthio)-3-methyloctanol,
2-(4,6-dimethoxy-2-pyridminylthio)-3,5,5-trimethylhexanol,
2-(4,6-dimethoxy-2-pyrimidinylthio)decanol,
2-(4,6-dimethoxy-2-pyrimidinylthio)-3-methylnonanol,
2-(4,6-dimethoxy-2-pyrimidinylthio)undecanol,
2-(4,6-dimethoxy-2-pyrimidinylthio)-3-methyldecanol,
3-cyclopentyl-2-(4,6-dimethoxy-2-pyrimidinylthio)propanol,
3-cyclopentyl-2-(4,6-dimethoxy-2-pyrimidinylthio)butanol,
3-cyclohexyl-2-(4,6-dimethoxy-2-pyrimidinylthio)propanol,
3-cyclohexyl-2-(4,6-dimethoxy-2-pyrimidinylthio)butanol,
2-cyclopentyl-2-(4,6-dimethoxy-2-pyrimidinylthio)ethanol,
2-cyclohexyl-2-(4,6-dimethoxy-2-pyrimidinylthio)ethanol,
2-cyclopropyl-2-(4,6-dimethoxy-2-pyrimidinylthio)ethanol,
3-cyclopropyl-2-(4,6-dimethoxy-2-pyrimidinylthio)butanol,
2-(4,6-dimethoxy-2-pyrimidinylthio)-4,4,4-trifluorobutanol,
3-cyclopropyl-2-(4,6-dimethoxy-2-pyrimidinylthio)-3-methylbutanol,
4-bromo-2-(4,6-dimethoxy-2-pyrimidinylthio)butanol,
2-(4,6-dimethoxy-2-pyrimidinylthio)-3,4,4,4-tetrafluorobutanol,
2-(4,6-dimethoxy-2-pyrimidinylthio)-3-phenylpropanol,
2-(4,6-demethoxy-2-pyrimidinylthio)-3-phenylbutanol,
3-(4-chlorophenyl)-2-(4,6-dimethoxy-2-pyrimidinylthio)propanol,
3-(4-chlorophenyl)-2-(4,6-demethoxy-2-pyrimidinylthio)butanol,
3-(4-tert.butylphenyl)-2-(4,6-dimethoxy-2-pyrimidinylthio)propanol,
3-(2-chlorophenyl)-2-(4,6-dimethoxy-2-pyrimidinylthio)butanol,
2-(4,6-dimethoxy-2-pyrimidinylthio)-4-phenylpentanol,
2-(4,6-dimethoxy-2-pyrimidinylthio)-3-(2,6-dimethylphenyl)propanol,
2-(4,6-dimethoxy-2-pyrimidinylthio)-3-ethylpentanol,
2-(4,6-dimethoxy-2-pyrimidinylthio)-3-ethyl-3-methylpentanol,
2-(4,6-dimethoxy-2-pyrimidinylthio)-3,3-dimethylhexanol,
2-(4,6-dimethoxy-2-pyrimidinylthio)-3,3-dimethylpentanol,
2-(4,6-dimethoxy-2-pyrimidinylthio)-3,3-dimethyl-5-phenylpentanol,
2-(4,6-dimethoxy-2-pyrimidinylthio)-3-phenylpentanol,
2-(4,6-dimethoxy-2-pyrimidinylthio)-4-methyl-3-phenylpentanol,
2-(4,6-dimethoxy-2-pyrimidinylthio)-3-methyl-3-phenylbutanol,
2-(4,6-dimethoxy-2-pyrimidinylthio)-3-methyl-3-phenylpentanol,
2-(4,6-dimethoxy-2-pyrimidinylthio)-3-ethyl-3-phenylpentanol,
3-(2-chlorophenyl)-2-(4,6-dimethoxy-2-pyrimidinylthio)-3-methylbutanol,
3-(3-chlorophenyl)-2-(4,6-dimethoxy-2-pyrimidinylthio)-3-methylbutanol,
2-(4,6-dimethoxy-2-pyrimidinylthio)-4-phenylbutanol,
2-(4,6-dimethoxy-2-pyrimidinylthio)-3,3-dimethyl-4-phenylbutanol,
3-(4-chlorophenyl)-2-(4,6-dimethoxy-2-pyrimidinylthio)-3-methylbutanol,
3-(4-bromophenyl)-2-(4,6-dimethoxy-2-pyrimidinylthio)-3-methylbutanol,
2-(4,6-dimethoxy-2-pyrimidinylthio)-3-methyl-3-(2-methylphenyl)butanol,
2-(4,6-dimethoxy-2-pyrimidinylthio)-3-methyl-3-(3-methylphenyl)butanol,
2-(4,6-dimethoxy-2-pyrimidinylthio)-3-methyl-3-(4-methylphenyl)butanol,
2-(4,6-dimethoxy-2-pyridmiinylthio)-3-methyl-3-(4-nitrophenyl)butanol,
2-(4,6-dimethoxy-2-pyrimidinylthio)-2-(1-phenylcyclopentyl)ethanol,
3-(3-bromophenyl)-2-(4,6-dimethoxy-2-pyrimidinylthio)-3-methylbutanol,
2-(4,6-dimethoxy-2-pyrimidinylthio)-3-(2-fluorophenyl)-3-methylbutanol,
2-(4,6-dimethoxy-2-pyrimidinylthio)-3-(4-fluorophenyl)-3-methylbutanol,
3-(2,6-dichlorophenyl)-2-(4,6-dimethoxy-2-pyrimidinylthio)propanol,
2-(4,6-dimethoxy-2-pyrimidinylthio)-3-(2-methylphenyl)propanol, 3-(2,4-dichlorophenyl)-2-(4,6-dimethoxy-2-pyrimidinylthio)-3-methylbutanol,
2-(4,6-dimethoxy-2-pyrimidinylthio)-3-(2-methylphenyl)butanol,
3-(3,4-dichlorophenyl)-2-(4,6-dimethoxy-2-pyrimidinylthio)-3-methylbutanol,
3-(3,4-difluorophenyl)-2-(4,6-dimethoxy-2-pyrimidinylthio)-3-methylbutanol,
3-(2,5-difluorophenyl)-2-(4,6-dimethoxy-2-pyrimidinylthio)-3-methylbutanol,
2-(4,6-dimethoxy-2-pyrimidinylthio)-3-(2,5-dimethylphenyl)-3-methylbutanol,
3-(2,6-diethylphenyl)-2-(4,6-dimethoxy-2-pyrimidinylthio)butanol,
2-(4,6-dimethoxy-2-pyrimidinylthio)-2-(trifluoromethylphenyl)-3-methylbutanol,
2-(4,6-dimethoxy-2-pyrimidinylthio)-3-(3-fluorophenyl)-3-methylbutanol,
2-(4,6-dimethoxy-2-pyrimidinylthio)-3-(2-naphthyl)-3-methylbutanol,
3-cyclopropyl-2-(4,6-dimethoxy-2-pyrimidinylthio)-propanol,
2-(4,6-dimethoxy-2-pyrimidinylthio)-2-(3-methylcyclopentyl)ethanol,
2-(4,6-dimethoxy-2-pyrimidinylthio)-2-(2,4-dimethylcyclopentyl)ethanol,
2-cyclobutyl-2-(4,6-dimethoxy-2-pyrimidinylthio)ethanol,
4-chloro-2-(4,6-dimethoxy-2-pyrimidinylthio)butanol,
2-[4,6-bis(difluoromethoxy)2-pyrimidinylthio]-3-methylbutanol,
2-(4-methyl-6-trifluoromethyl-2-pyrimidinylthio)-3-methylbutanol,
2-(4-chloro-6-methoxy-2-pyrimidinylthio)-3-methylbutanol,
2-cyclopropyl-2-(4,6-dimethoxy-2-pyrimidinylthio)acetaldehyde,
2-(4,6-dimethoxy-2-pyrimidinylthio)-2-(1-methylcyclopropyl)acetaldehyde,
2-(4,6-dimethoxy-2-pyrimidinylthio)-2-(1-methylcyclopropyl)ethanol,
2-(4,6-dimethoxy-2-pyrimidinylthio)-2-(1-methylcyclopentyl)acetaldehyde,
2-(4,6-dimethoxy-2-pyrimidinylthio)-2-(1-methylcyclopentyl)ethanol,
2-(4,6-dimethoxy-2-pyrimidinylthio)-2-(1-methylcyclohexyl)acetaldehyde,
2-(4,6-dimethoxy-2-pyrimidinylthio)-2-(1-methylcyclohexyl)ethanol,
3-cyclopropyl-2-(4,6-dimethoxy-2-pyrimidinylthio)-butyraldehyde,
3-cyclopropyl-2-(4,6-methoxy-2-pyrimidinylthio)-3-methylbutyraldehyde,
3-cyclopentyl-2-(4,6-dimethoxy-2-pyrimidinylthio)-3-methylbutyraldehyde,
3-cyclopentyl-2-(4,6-dimethoxy-2-pyrimidinylthio)-3-methylbutanol,
3-cyclohexyl-2-(4,6-dimethoxy-2-pyrimidinylthio)-3-methylbutyraldehyde,
3-cyclohexyl-2-(4,6-dimethoxy-2-pyrimidinylthio)-3-methylbutanol,
2-(4,6-dimethoxy-2-pyrimidinylthio)-4,4-dimethylvaleraldehyde,
2-(4,6-dimethoxy-2-pyrimidinylthio)-4,4-dimethylpentanol,
2-(4,6-dimethoxy-2-pyrimidinylthio)-3,3-dimethyloctanol,
3,3-diethyl-2-(4,6-dimethoxy-2-pyrimidinylthio)-valeraldehyde,
3,3-diethyl-2-(4,6-dimethoxy-2-pyrimidinylthio)pentanol,
4-chloro-2-(4,6-dimethoxy-2-pyrimidinylthio)-3,3-dimethylbutyraldehyde,
4-chloro-2-(4,6-dimethoxy-2-pyrimidinylthio)-3,3-dimethylbutanol,
4-bromo-2-(4,6-dimethoxy-2-pyrimidinylthio)-3,3-dimethylbutyraldehyde,
4-bromo-2-(4,6-dimethoxy-2-pyrimidinylthio)-3,3-dimethylbutanol,
5,6-dichloro-2-(4,6-dimethoxy-2-pyrimidinylthio)hexaldehyde,
5,6-dichloro-2-(4,6-dimethoxy-2-pyrimidinylthio)hexanol,
3-(4-methoxyphenyl)-2-(4,6-dimethoxy-2-pyrimidinylthio)propionaldehyde, and
3-(4-methoxyphenyl)-2-(4,6-dimethoxy-2-pyrimidinylthio)propanol.

As the compounds of the formula (I), according to the invention, contain an asymmetric carbon atom in the structure, they can also occur in enantiomeric forms.

If use is made, in the above-mentioned process a), of 4,6-dimethoxy-2-mercapto-pyrimidine and 2-bromo-3-methylbutyraldehyde as starting materials, for exmaples, the course of the reaction can be represented by the following equation:

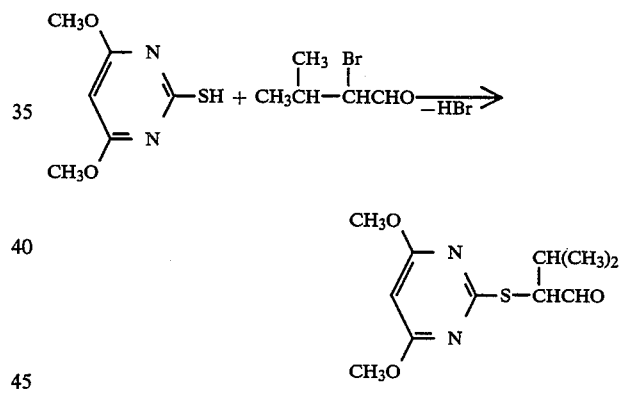

If use is made, in the above-mentioned process b), of 2-(4,6-dimethoxy-2-pyrimidinylthio)butanol as a starting material for example, the course of the reaction can be represented by the following equation:

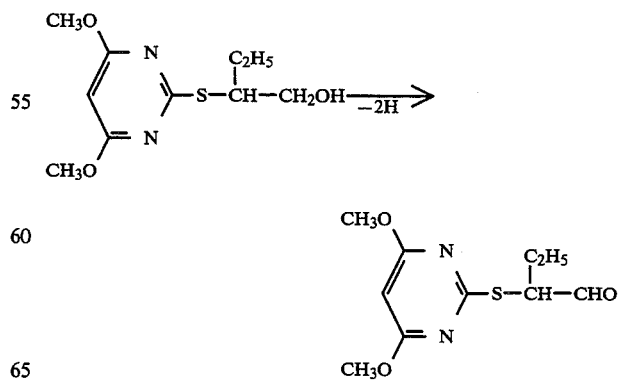

If use is made, in the above-mentioned process c), of 2-(4,6-dimethoxy-2-pyrimidinylthio)-3-methylbutyraldehyde as a starting material, for example, the course of the reaction can be represented by the following equation:

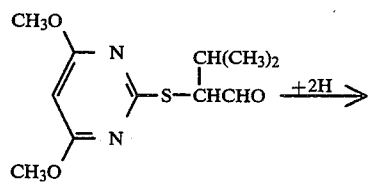

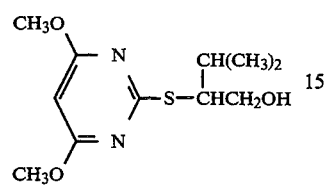

If use is made, in the above-mentioned process d), of 2-(4,6-dimethoxy-2-pyrimidinylthio)-3-methylbutyric acid as a starting material, for example, the course of the reaction can be represented by the following equiation:

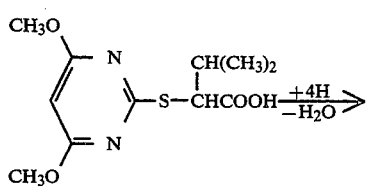

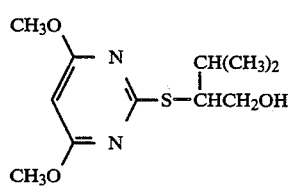

If use is made, furthermore, in the above-mentioned process d), of methyl 2-(4,6-dimethoxy-2-pyrimidinylthio)-3-methylbutyrate as a starting material, for example, the course of the reaction can be represented by the following equation:

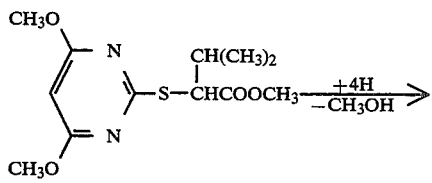

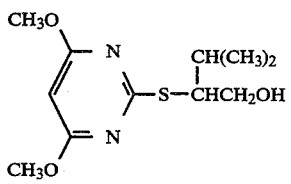

If use is made, in the above-mentioned process e), of 4,6-dimethoxy-2-methane sulfonylpyrimidine and 2-mercapto-3-methylbutanol, for example, the course of the reaction can be represented by the following equation:

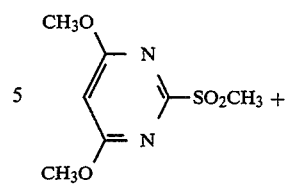

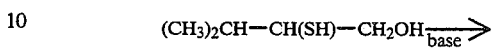

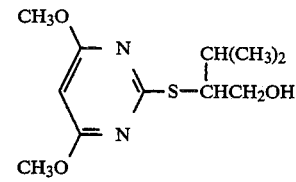

If use is made, in the above-mentioned process f), of 4,6-dimethoxy-2-mercapto-pyrimidine and 2-isopropyloxirane, for example, the course of the reaction can be represented by the following equation:

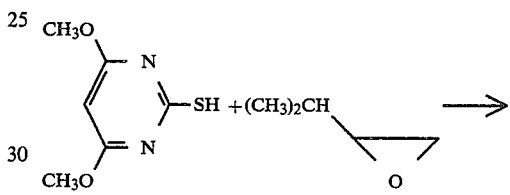

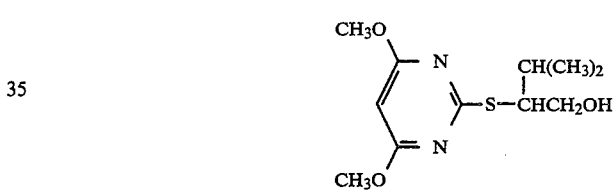

If use is made, in the above-mentioned process g) of 4,6-dimethoxy-2-mercapto-pyrimidine and 2-chloro-3-methylbutanol, for example, the course of the reaction can be represented by the following equation.

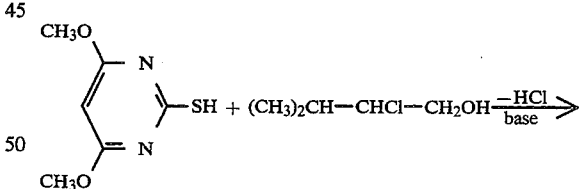

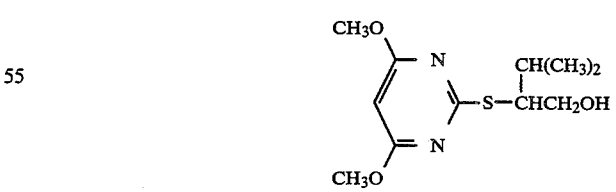

The compounds of the formula (II) are known and are described, for example, in Japanese Patent Laid-open No. Hei 3-135963.

As a specific preferred example of the compounds of formula (II), there can be mentioned: 4,6-dimethoxy-2-mercapto-pyrimidine.

The compounds of the formula (III) can, in general, be obtained when compounds of the formula (X)

$$R^3\text{-}CH_2CHO \qquad (X)$$

are reacted with halogen or halogenating agents.

The compounds of the formula (X) are well-known aldehydes in the field of organic chemistry and can be obtained by known methods.

As examples of halogen and halogenating agents, there can be mentioned: bromine and N-bromosuccinimide.

The compounds of the formula (III) can also easily be obtained by reacting the above compounds of the formula (X) with cuptic chloride.

In the process b), the compounds of the formula (Ia) are a part of the compounds of the formula (I), according to the invention, made by methods, according to the processes c), d), e), f) and g).

In the oxidation reaction of the process b), sulfoxides and either acid anhydrides or acid chlorides can be used as oxidizing agents.

As an example of sulfoxides, dimethylsulfoxide can be mentioned.

As an example of acid anhydrides, there may be mentioned: acetic anhydride, trifluoroacetic anhydride, etc.

As an example of acid chlorides, oxalyl chloride can be mentioned.

The oxidation reaction, according to the process b), is carried out by two steps in which the compounds of the formula (Ia) are reacted with, for example, trifluoroacetic anhydride in the presence of dimethylsulfoxide, and then the products of said first step are reacted with a base in a second step.

In the above reaction, as an example of said base any tertiary amine, e.g. triethylamine, can be used.

In the process c), the compounds of the formula (Ib) are also a part of the compounds of the formula (I) according to the invention, made by the methods, according to the processes a) and b).

As examples of a reducing agent, there can be mentioned: sodium boron hydride, lithium aluminum hydride, di-isobutyl aluminum hydride, etc.

In carrying out the process a) mentioned above, use may be made, as suitable diluents, of any inert solvent.

Examples of such diluents are water, aliphatic, cycloaliphatic and aromatic, optionally chlorinated, hydrocarbons such as hexane, cyclohexane, petroleum ether, ligroin, benzene, toluene, xylene, methylene chloride, chloroform, carbon tetrachloride, ethylene chloride, chlorobenzene, and the like; ethers such as diethyl ether, methyl ethyl ether, di-isopropyl ether, dibutyl ether, dioxane, tetrahydrofuran, and the like: ketones such as acetone, methylethyl ketone, methyl-iso-propyl ketone, methyl-iso-butyl ketone, and the like; nitriles such as acetonitrile, propionitrile, acrylonitrile, and the like; alcohols such as methanol, ethanol, iso-propanol, butanol, ethylene glycol, and the like; esters such as ethyl acetate and amyl acetate; acid amides such as dimethyl formamide, dimethyl acetamide, and the like; sulfones and sulfoxides such as dimethyl sulfoxide, sulfolane, and the like; and bases such as pyridine.

The above-mentioned process a) is carried out preferably in the presence of an acid binder, for example, a hydroxide, carbonate, bicarbonate or alcoholate of an alkali metal, or a tertiary amine, such as triethylamine, diethylaniline, pyridine, 4-dimethylamino pyrimidine, 1,4-diazabicyclo-[2,2,2]octane(DABCO) or 1,8-diazabicyclo[5,4,0]undec-7-ene(DBU).

In the above-mentioned process a), the reaction temperature can be varied within a substantially wide range. In general, the reaction is carried out at a temperature from about −80° C. to about 150° C., preferably from about −10° C. to about 100° C.

Further, the reaction is carried out under normal pressure, although it is also possible to employ elevated or reduced pressure.

In carrying out the process a), for example, about 0.1 to 1.5 moles of the compounds of the formula (III) may be employed pe mole of the compounds of the formula (II) in the presence of an inert solvent such as acetonitrile and in the presence of potassium carbonate so as to obtain the desired compounds of the formula (I).

In carrying out the process b), use may be made, as suitable diluents, of the same solvents as mentioned in the process a), with the exception of water and alcohols.

In the process b), the reaction temperature can be varied within a substantially wide range. In general, the reaction is carried out at a temperature from about −78° C. to about 30° C., preferably from about −78° C. to about 0°.

Further, the reaction is carried out under normal pressure, although it is also possible to employ elevated or reduced pressure.

In carrying out the process c) use may be made, as suitable diluents, of the same solvents as mentioned in the process a), with the exception of methylene chloride, chloroform, propyleneoxide and ketones.

In the process c), the reaction temperature can be varied within a substantially wide range. In general, the reaction is carried out from about −100° C. to about 80° C., preferably from about −78° C. to about 40° C.

Further, the reaction is carried out under normal pressure, although it is also prossible to employ elevated or reduced pressure.

In carrying out the process c), as specifically given in an example hereinafter, the compounds of the formula (IB) are reduced by sodium boron hydride to obtain the desired compounds of the formula (I).

The compounds of the formula (Ia) can easily be obtained by method c), and also by alternative methods, namely the aforemenioned processes d), e), f) and g).

In the process d), the compounds of the formula (IV) are known and described in Japanese Patent Laid-open No. 85262/1990.

In the process d), where $R^4$ is hydrogen in the formula (IV), borane and complexes thereof are examples of reducing agents and, where $R^4$ is alkyl, then the same reducing agents as mentioned in the process c) can be used.

In carrying out the process d), where $R^4$ is hydrogen in the formula (IV), then use may be made, as suitable diluents, for the same solvents as mentioned in the process a), with the exception of water, methylene chloride, chloroform, carbon tetrachloride, ethylene chloride, ketones, nitriles and alcohols, and where $R^4$ is alkyl in the formula (IV), then use may be made, as suitable diluents, of the same solvents as mentioned in the process c).

In the process e), the compounds of the formula (V) are known and described in Japanese Patent Laid-open No. 169868/1991.

The compounds of the formula (VI) can easily be made by a conventional method and include known compounds.

In carrying out the process e), use may be made, as suitable diluents, of the same solvents as mentioned in the process c).

The process e) can be carried out in the presence of a base, and as a specific example of a base, calcium carbonate can be mentioned.

In the processes f) and g), the compounds of the formula (VII) are known, and the compounds of the formulae (VIII) and (IX) can easily be obtained by conventional methods.

In carrying out the process f), use may be made, as suitable diluents, of the same solvents as mentioned in the process a), with the exception of water, hexane, cyclohexane, petroleum ether, ligroin, alcohols such as methanol, ethanol, isopropanol and ethylene glycol, and bases.

The reaction, according to the process f), can be carried out in the presence of acid catalysts, including Lewis acid such as toluene sulfonic acid, trifluoroborane ethylate, and the like.

In carrying out the process g), use may be made, as suitable diluents, of the same solvents as mentioned in the process a).

In the process d), where $R^4$ is hydrogen in in the formula (IV), then the reaction is carried out at a temperature from about $-100°$ C. to about $30°$ C., preferably from $-78°$ C. to about $-40°$ C. and where $R^4$ is alkyl in the formula (IV), then the reaction is carried out at a temperature from about $-100°$ C. to about $150°$ C., preferably from about $-78°$ C. to about $50°$ C.

In the processes e) and f), the reaction is carried out at a temperature from about $-40°$ C. to about $150°$ C., preferably from about $10°$ C. to about $80°$ C.

In the process g), the reaction is carried out at a temperature from about $-40°$ C. to about $150°$ C., preferably from about $20°$ C. to about $80°$ C.

The reactions, according to the processes d), e), f) and g) are carried out under normal pressure, although it is also possible to employ elevated or reduced pressure.

The active compounds according to the invention can be used as defoliants, desiccants, agents for destroying broad-leaved plants and, especially, as weedkillers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Seteria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Arena, Secale, Sorghum, Panicum, Saccharum, Ananas, Asparagus and Alium.

However, the use of the active compounds according to the invention is in no way restricted to these general, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforstations, decorative tree plantings, orchards, vineyards, citrus groves, nut orchards, banana plantations, coffee plantations, tea plantations, rubber plantations, oil palm plantations, cocoa plantations, soft fruit plantings in and hop fields, and for the selective combating of weeds in annual cultures.

The active compounds can be converted into the customary formulations, such as solutions, emulsions, wettable powders, suspensions, powders, foams, pastes, granules, aerosols, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquified gaseous or solid diluents or carriers, optionally with the use of surface-active agents, that is to say emulsifying agents and/or dispersing agents and/or foam-forming agents. In the case of the use of water and an extender, organic solvents can, for example, also be used as auxiliary solvents.

As liquid solvents diluents or carriers, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, alphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethyl-sulphoxide, as well as water.

By liquified aqueous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid ethers, for example alkyl-aryl polyglycol ethers alkyl sulphonates, alkyl sulphates, aryl sulphonates as well as albumin hydrolysis products. Dispersing agents include, for example, lignin sulphite waste liquors and methylcellulose.

Adhesives such as caroxymethylcellulose and natural and synthetic polymers in the form of powders, granules or lattices, such as gum arabic, polyvinyl alcohol and polyvinyl acetate, can be used in the formulation.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts or iron, manganese, boron, copper, cobalt, molybdenum and zinc.

The formulations in general contain from 01 to 95 per cent by weight of active compound, preferably 0.5 to 90 percent by weight.

The active compounds according to the invention, as such or in the form of their formulations, can also be used, for combating weeds, as mixtures with known herbicides, finished formulations or tank mixes being possible.

Possible components for the mixtures are known herbicides, such as, for example, 4-amino-6-(1,1-dimethylethyl)-3-ethylthio-1,2,4-triazin-5(4H)-one, 1-amino-6-ethylthio-3-(2,2-dimethylpropyl)-1,3,5-triazine-2,4(1H,3H)-dione or N-(2-benzothiozolyl)-N,N'-dimethyl-urea, for combating weeds in cereals; 4-amino-3-methyl-6-phenyl-1,2,4-triazin-5(4H)-one for combating weeds in sugar beet cultures and 4-amino-6-(1,1-dimethylethyl)-3-methylthio-1,2,4-triazin-5(4H)-one for combating weeds in soy-bean cultures. Surprisingly, some mixtures also show a synergistic action.

Mixtures with other known active compounds, such as herbicides, fungicides, insecticides, acaricides, nematicides, bird repellents, plants nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants.

They can also be incorporated into the soil before sowing. They are used, in particular, after emergence of the plants.

The amount of active compound used can vary within a substantial range. It depends essentially on the nature of the desired effect. In general, the amounts used are between 0.01 and 4 kg of active compound per hectare of soil surface, preferably between 0.05 and 2 kg per ha.

The preparation and use of he active compounds according to the invention can be seen from the following examples.

SYNTHESIS EXAMPLE

Example 1

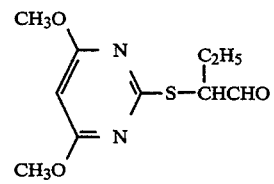

Oxalyl chloride (1.3 g) was dissolved in methylene chloride (50 ml), and at −60° C., a solution of dimethylsulfoxide (0.85 g) in methylene chloride (10 ml) was added dropwise to the solution. In addition, at −60° C., a solution of 2-(4,6-dimethoxy-2-pyrimidinylthio)-butanol (2 g) in methylene chloride (20 ml) was added dropwise to the reaction mixture. THe mixture was stirred for 30 minutes, and then at −60° C., triethylamine (2.5 g) was added dropwise.

Thereafter the mixture was gradually warmed at room temperature.

The reaction mixture was washed with water and the organic layer was dried over anhydrous sodium sulfate. The sulfate was evaporated under reduced pressure.

The residue was purified by column chromatography (eluent: hexane/ethyl acetate) to give the desired 2-(4,6-dimethoxy-2-pyrimidinylthio)butyraldehyde (1.2 g). $n^{20}_D 1.5452$.

Example 2

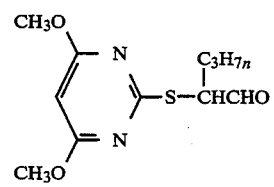

To an acetonitrile solution (50 ml) of 2-bromo-3-valeraldehyde (3.8 g) and 4,6-dimethoxy-2-mercaptopyrimidine (4.0 g) was added potassium carbonate followed by heat-refluxing for one minute. After undissolved substances have been filtered off, the acetonitrile was distilled off under reduced pressure, and the residue was dissolved in toluene and undissolved substances removed therefrom. Thereafter, the toluene was distilled off from the reaction product to obtain the desired 2-(4,6-dimethoxy-2-pyrimidinylthio)3-valeraldehyde (5.9 g). $n_D^{20} 1.5432$.

Example 3

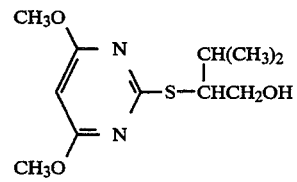

To a methanol solution of 2-(4,6-dimethoxy-2-pyrimidinylthio)-methyl butyraldehyde (1.5 g) was added sodium boron hydride (0.2 g), followed by a five-minute stirring at room temperature. Water was then added to the reaction liquid, followed by extraction with ethyl acetate, water-washing of the resulting organic layer and drying thereof in that order. After the removal of the drying agent from the reaction product under filtration, followed by separation of ethyl acetate under reduced pressure distillation, there was obtained an oily substance that was then purified by silica gel column chromatography to obtain the desired 2-(4,6-dimethoxy-2-pyrimidinylthio)-3-methylbutanol (1.3 g) $n^{20}_D 1.5445$.

Example 4

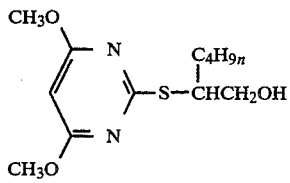

A tetrahydrofuran solution of methyl 2-(4,6-dimethoxy-2-Pyrimidinylthio)-hexanoate (3.2 g) was added dropwise to a tetrahydrofuran suspension of aluminum lithium hydride (0.7 g) under ice-cooling, followed by 30 minutes stirring at room temperature, addition thereto of water and removal therefrom of precipitates by filtration. Then tetrahydrofuran was distilled off form the reaction liquid under reduced pressure and the resulting residue was subjected to silica gel column chromatography, to obtain the desired 2-(4,6-dimethoxy-2-pyrimidinylthio)hexanol (2.7 g). $n_D$ 1.5303.

The compounds of the formula (I) which can be prepared in the same way as in the above examples are shown in Table 1, including the compounds of Example 1 to 4.

TABLE 1

| Compd. No. | $R^1$ | $R^2$ | $R^3$ | $-CH\begin{smallmatrix}A\\B\end{smallmatrix}$ | $n_D^{20}$ |
|---|---|---|---|---|---|
| 1 | CH$_3$O | CH$_3$O | C$_2$H$_5$ | CHO | 1.5452 |
| 2 | " | " | C$_3$H$_7$-n | CHO | 1.5432 |
| 3 | " | " | C$_3$H$_7$-iso | CH$_2$OH | 1.5279 |
| 4 | " | " | C$_4$H$_9$-n | CH$_2$OH | 1.5303 |
| 5 | " | " | —(CH$_2$)$_5$CH$_3$ | CHO | 1.5239 |
| 6 | " | " | —(CH$_2$)$_6$CH$_3$ | CHO | 1.5175 |
| 7 | " | " | —⟨phenyl⟩ | CHO | 1.5993 |
| 8 | " | " | C$_2$H$_5$ | CH$_2$OH | 1.5488 |
| 9 | " | " | C$_3$H$_7$-n | " | 1.5393 |
| 10 | " | " | C$_3$H$_7$-iso | " | 1.5445 |
| 11 | " | " | C$_4$H$_9$-n | " | 1.5345 |
| 12 | CH$_3$O | CH$_3$O | C$_4$H$_9$-tert | CH$_2$OH | 1.5078 |
| 13 | " | " | C$_6$H$_{13}$-n | " | 1.5188 |
| 14 | " | " | C$_7$H$_{15}$-n | " | 1.5078 |
| 15 | " | " | CH$_2$(CF$_2$)$_6$F | " | Sticky solid |
| 16 | " | " | CH$_2$—⟨phenyl⟩ | " | 1.5852 |
| 17 | " | " | C$_5$H$_{11}$-n | " | 1.5298 |
| 18 | " | " | CH$_3$ | CHO | 1.5560 |
| 19 | " | " | (CH$_2$)$_4$CH$_3$ | " | 1.5277 |
| 20 | " | " | C$_4$H$_9$-tert | " | 1.5216 |
| 21 | " | " | CH$_2$—⟨H⟩ | " | 1.5330 |

TABLE 1-continued $$\text{(I)}$$

Structure (I): Pyrimidine with $R^1$ at 4-position, $R^2$ at 6-position, and at 2-position: $-S-CH(R^3)-CH(A)(B)$

| Compd. No. | $R^1$ | $R^2$ | $R^3$ | —CH(A)(B) | $n_D^{20}$ |
|---|---|---|---|---|---|
| 22 | " | " | CH(CH₃)–C₆H₅ | " | 1.5783 |
| 23 | " | " | C(CH₃)₂–C₆H₅ | " | 1.5708 |
| 24 | CH₃ | CH₃ | C₃H₇-iso | " | 1.5470 |
| 25 | CH₃O | CH₃O | C₄H₉-iso | CH₂OH | 1.5246 |
| 26 | CH₃O | CH₃O | C₅H₁₁-n | CH₂OH | 1.5298 |
| 27 | " | " | CH₂–cyclohexyl | " | 1.5211 |
| 28 | " | " | C(CH₃)₂–C₆H₅ | " | 1.5635 |
| 29 | " | " | C₄H₉-sec | CHO | 1.5397 |
| 30 | " | " | C₄H₉-iso | " | 1.5320 |
| 31 | " | " | cyclohexyl | " | 1.5428 |
| 32 | " | " | (CH₂)₂CHCH₂Cl, Cl | " | 1.5611 |
| 33 | " | " | CH₂–C₆H₅ | " | " |
| 34 | " | " | CH₂–C₆H₄–OCH₃ (p) | " | 1.5808 |
| 35 | " | " | C₄H₉-sec | CH₂OH | 1.5342 |
| 36 | " | " | cyclopentyl | " | |
| 37 | " | " | cyclohexyl | " | 1.5343 |

TABLE 1-continued

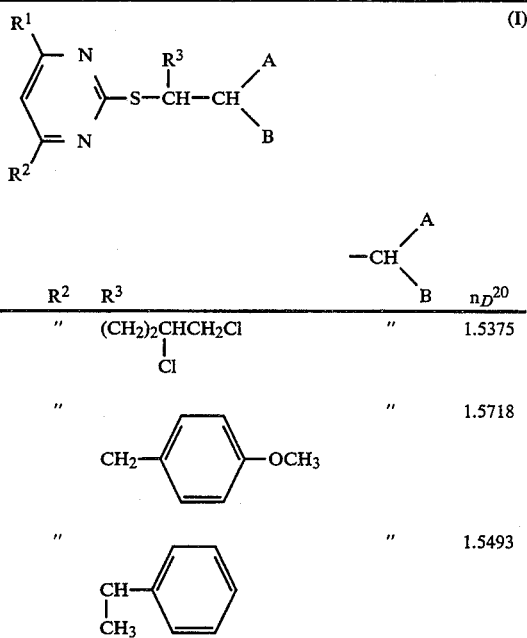

| Compd. No. | R$^1$ | R$^2$ | R$^3$ | $-CH\begin{smallmatrix}A\\B\end{smallmatrix}$ | n$_D^{20}$ |
|---|---|---|---|---|---|
| 38 | " | " | (CH$_2$)$_2$CHCH$_2$Cl<br>           \|<br>           Cl | " | 1.5375 |
| 39 | " | " | CH$_2$—C$_6$H$_4$—OCH$_3$ | " | 1.5718 |
| 40 | " | " | CH(CH$_3$)—C$_6$H$_5$ | " | 1.5493 |

Background Example (synthesis of a starting material)

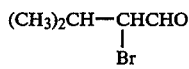

To a solution of 3-methylbutyraldehyde (20.0 g) in ether (200 ml) bromine (37.2 g) was added dropwise while the internal temperature was kept at 5° to 10° C. After the reaction was completed, the resulting ether layer was washed with a saturated solution of sodium chloride, sodium bicarbonate, water and again water, in that order, followed by drying. Upon removal of the ether by distillation the desired 2-bromo-3-methyl-butyraldehyde (30.4 g) was obtained. n$_D^{20}$1.4731.

Biotest Examples

There follow tests for determining the herbicidal activity of the compounds of the present invention:

Test Example 1

Pre-emergence soil treatment test on upland weeds

Formulation of Active Compounds

Carrier: 5 parts by weight of acetone

Emulsifier: 1 part by weight of benzyloxy polyglycol ether

To produce a suitable formulation each of the active compounds, 1 part by weight of each of the active compounds according to the present invention was mixed with the stated amount of carrier and the stated amount of emulsifier, and the resulting emulsifiable concentrate was then diluted with water to the desired concentrations.

Test Procedures

In a greenhouse, a number of tests pots each having an area of 120 cm$^2$ were charged with soil taken out from a cultivated field. Onto the soil surfaces in the respective test pots were sown the seeds of Barnyard grass (*Echinochloa crus-galli*) and Redroot pigweed (*Amaranthus retroflexus*), respectively, followed by soil covering thereon.

Thereafter, predetermined dosages of the active compound formulations mentioned above were uniformly sprayed onto the soil surfaces of the respective test pots.

Four weeks after the application of the active compound formulations, the degrees of herbicidal effect on the weeds were determined based on the following assessment:

A herbicidal effect of 100% was rated as "completely killed" and the determined degrees of herbicidal effects were rated under the corresponding percentage.

In this test the active compounds as claimed in the present application, for example compounds 1, 2, 3, 6, 8, 9, 10, 11, 12, 16 and 20, showed herbicidal activities against Barnyard grass and Redroot Pigweed between 95 and 100%.

Test Example 2

Post-emergence foliage treatment on upland weeds

In a greenhouse, a number of test pots each having an area of 120 cm$^2$ were charged with soil taken out from a cultivated field. Seeds of Barnyard grass and Redroot pigweed, respectively, were sown onto the soil surfaces in the respective test pots, followed by cultivation for ten days.

Thereafter, predetermined dosages of the active compound formulations prepared as in Test Example 1 mentioned above were uniformly sprayed onto the foliage portions of the test weeds in the respective test pots.

Three weeks after the spraying of the active compound formulations, the degrees of the herbicidal effect on the weeds were determined.

In this test compounds as claimed in the present application, for example compounds 1, 2, 3, 6, 8, 9, 10, 11, 12, 15 and 20, showed herbicidal activities against Barnyard grass and Redroot Pigweed between 95 and 100%.

It will be appreciated that the instant specification and claims are set forth by way of illustration and not limitation, and that various modifications and changes

What is claimed is:

1. A pyrimidinylthioalkane derivative of the formula

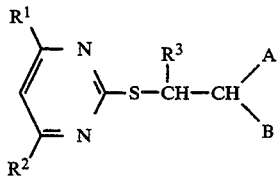

wherein
   $R^1$ represents $C_1$-$C_4$-alkyl, $C_1$-$C_4$-alkoxy, halo, $C_1$-$C_4$-haloalkyl or $C_1$-$C_4$-haloalkoxy,
   $R^2$ represents $C_1$-$C_4$-alkyl, $C_1$-$C_4$-alkoxy, halo, $C_1$-$C_4$-haloalkyl or $C_1$-$C_4$-haloalkoxy,
   $R^3$ represents straight chain or branched $C_1$-$C_{30}$-alkyl optionally substituted by $C_3$-$C_8$-cycloalkyl, halogen, naphthyl or optionally substituted phenyl; phenyl optionally substituted by halogen, $C_1$-$C_4$-alkyl, $C_1$-$C_4$-haloalkyl, nitro or cyano; naphthyl; or $C_3$-$C_8$-cycloalkyl, and
   A represents hydroxy, and
   B represents hydrogen, or
   A and B together=O.

2. A compound according to claim 1, wherein
   $R^1$ represents $C_1$-$C_3$-alkyl, $C_1$-$C_3$-alkoxy, fluorine, chlorine, bromine, iodine, $C_1$-$C_3$-haloalkyl or $C_1$-$C_3$-haloalkoxy,
   $R^2$ represents $C_1$-$C_3$-alkyl, $C_1$-$C_3$-alkoxy, fluorine, chlorine, bromine, iodine, $C_1$-$C_3$-haloalkyl or $C_1$-$C_3$-haloalkoxy,
   $R^3$ represents straight chain or branched $C_1$-$C_{12}$-alkyl optionally substituted by $C_3$-$C_6$-cycloalkyl, fluorine, chlorine, bromine, $C_1$-$C_4$-alkylphenyl, halophenyl, or $C_{1-4}$-alkoxyphenyl, phenyl which is optionally substituted by $C_1$-$C_4$-alkyl, halogen, or $C_1$-$C_4$-haloalkyl (wherein halo is chlorine or bromine), nitro or cyano; or $C_3$-$C_6$-cycloalkyl, and
   A represents hydroxy, and
   B represents hydrogen, or
   A and B together are=O.

3. A compound according to claim 1, wherein
   $R^1$ represents methyl, ethyl, ethoxy, fluorine, chlorine, bromine, trichloromethyl, trifluoromethyl, chloromethoxy, difluoromethoxy or trifluoromethoxy,
   $R^2$ represents methyl, ethyl, methoxy, ethoxy, fluorine, chlorine, bromine, trichloromethyl, trifluoromethyl, chloromethoxy, difluoromethoxy or trifluoromethoxy,
   $R^3$ represents straight chain or branched $C_1$-$C_{10}$-alkyl optionally substituted by $C_3$-$C_6$-cycloalkyl, fluorine, chlorine, bromine, chlorophenyl, $C_1$-$C_4$-alkylphenyl, or methoxyphenyl; phenyl optionally substituted by $C_1$-$C_4$-alkyl, chlorophenyl, $C_1$-$C_3$-haloalkyl or nitro; or $C_5$-$C_6$-cycloalkyl, and
   A represents hydroxy, and
   B represents hydrogen, or
   A and B together are=0.

4. A compound according to claim 1, wherein
   $R^1$ and $R^2$ are methoxy,
   $R^3$ represents straight chain or branched $C_{1-9}$-alkyl optionally substituted by at least one member selected from the group consisting of cyclopropyl, cyclopentyl, cyclohexyl, fluorine, chlorine, bromine, chlorophenyl, $C_1$-$C_4$-alkylphenyl and methoxyphenyl; phenyl optionally substituted by one or more of methyl, t-butyl, chlorine, trifluoromethyl and nitro; cyclopentyl; or cyclohexyl, and
   A is hydroxy and
   B is hydrogen, or
   A and B together are=0.

5. A compound according to claim 1, wherein such compound is

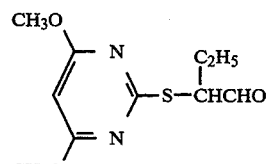

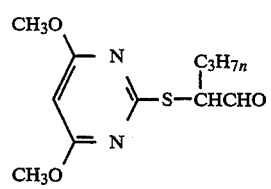

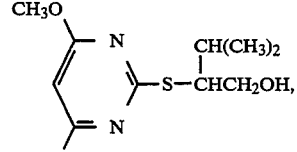

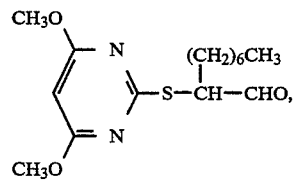

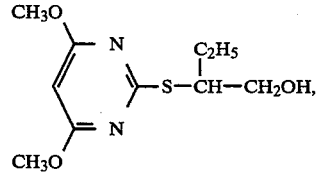

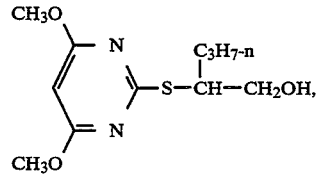

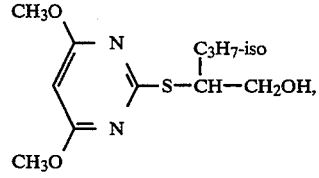

-continued

[Structure: 4,6-dimethoxypyrimidin-2-yl-S-CH(C4H9-n)-CH2OH]

[Structure: 4,6-dimethoxypyrimidin-2-yl-S-CH(C4H9-tert)-CH2OH]

-continued

[Structure: 4,6-dimethoxypyrimidin-2-yl-S-CH(CH2-phenyl)-CH2OH]

or

[Structure: 4,6-dimethoxypyrimidin-2-yl-S-CH(C4H9-tert)-CHO]

6. A herbicidal composition comprising a herbicidally effective amount of a compound according to claim 1 and a diluent.

7. A method of combating unwanted vegetation which comprises applying to such vegetation or to a locus from which it is desired to exclude such vegetation a herbicidally effective amount of a compound according to claim 1.

8. A method of combating unwanted vegetation which comprises applying to such vegetation or to a locus from which it is desired to exclude such vegetation a herbicidally effective amount a compound according to claim 4.

* * * * *